(12) United States Patent
Manishen

(10) Patent No.: US 7,766,008 B2
(45) Date of Patent: Aug. 3, 2010

(54) ENDOSCOPIC BITE BLOCK SYSTEM

(76) Inventor: Wayne J. Manishen, 225 Grenfell Boulevard, Winnipeg (CA) MB R3P 0B8

( * ) Notice: Subject to any disclaimer, the term of this patent is extended or adjusted under 35 U.S.C. 154(b) by 979 days.

(21) Appl. No.: 11/536,253

(22) Filed: Sep. 28, 2006

(65) Prior Publication Data

US 2007/0225570 A1    Sep. 27, 2007

Related U.S. Application Data

(60) Provisional application No. 60/785,925, filed on Mar. 27, 2006.

(51) Int. Cl.
| | |
|---|---|
| *A61M 16/00* | (2006.01) |
| *A61M 5/00* | (2006.01) |
| *A61M 5/32* | (2006.01) |
| *A61M 25/00* | (2006.01) |
| *A61M 31/00* | (2006.01) |
| *A61B 1/32* | (2006.01) |
| *A61F 11/00* | (2006.01) |

(52) U.S. Cl. .................. 128/200.26; 128/207.14; 128/207.15; 128/207.16; 128/207.17; 600/237; 600/238; 600/239; 600/240; 604/171; 604/179; 604/264; 604/270; 606/108

(58) Field of Classification Search ............ 128/200.26, 128/207.14, 207.15, 207.16, 207.17; 600/237, 600/238, 239, 240; 604/171, 179, 264, 270; 606/108
See application file for complete search history.

(56) References Cited

U.S. PATENT DOCUMENTS

| D283,158 | S | 3/1986 | Jackson | |
|---|---|---|---|---|
| 5,174,284 | A | 12/1992 | Jackson | |
| 6,517,549 | B1 * | 2/2003 | Dennis | ................ 606/108 |
| 2005/0090835 | A1 | 4/2005 | Deal et al. | |
| 2006/0272647 | A1 * | 12/2006 | Hauge | ............. 128/207.16 |

OTHER PUBLICATIONS

Canadian Patent Office, Notice of Allowance, Canadian Application No. 2,582,901, Jun. 6, 2008.
Manishen, Response to Canadian Office Action, Canadian Application No. 2,582,901, Jan. 21, 2008, 22 pages.
Canadian Patent Office, Canadian Office Action, Canadian Application No. 2,582,901, Jul. 27, 2007.

* cited by examiner

*Primary Examiner*—Patricia M Bianco
*Assistant Examiner*—Nihir Patel
(74) *Attorney, Agent, or Firm*—Neustel Law Offices

(57) ABSTRACT

An endoscopic bite block system for increasing the speed and efficiency of an endoscopic procedure. The endoscopic bite block system includes a base member including a central opening and at least one tube attachment, a channel member latitudinally extending from an outer edge of the central opening and a strap member removably attached to the base member, wherein the strap member removably attaches the base member to the mouth of the patient.

20 Claims, 5 Drawing Sheets

ENDOSCOPIC BITE BLOCK SYSTEM

CROSS REFERENCE TO RELATED APPLICATIONS

I hereby claim benefit under Title 35, United States Code, Section 119(e) of U.S. provisional patent application Ser. No. 60/785,925 filed Mar. 27, 2006. The 60/785,925 application is currently pending. The 60/785,925 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to medical instruments and more specifically it relates to an endoscopic bite block system increasing the speed and efficiency of an endoscopic procedure.

2. Description of the Related Art

Any discussion of the prior art throughout the specification should in no way be considered as an admission that such prior art is widely known or forms part of common general knowledge in the field.

Medical instruments have been in use for years. Typically, medical instruments vary greatly in configuration depending on what procedure that the medical instruments are utilized. One such procedure that medical instruments are utilized are endoscopic procedures.

During an endoscopic procedure a bite block tool is generally utilized to allow access to the interior of hollow organs, such as but not limited to the esophagus, stomach or respiratory tract. The bite block tool prevents patients from biting down on the medical instruments, wherein the medical instruments are generally very expensive. Generally bite block tools include a center main opening to allow entrance of the endoscope and at least one side opening to allow easier breathing for the patient.

While performing an endoscopic procedure it is generally required that a physician assistant must hold a suction catheter in the patient's mouth to accumulate excessive saliva. During this time the physician assistant must also perform many other duties, wherein steadily holding the suction catheter can become a nuisance and also very difficult. The suction catheter may easily fall out of the patient's mouth during the endoscopic procedure which can greatly slow down the endoscopic procedure and cause discomfort for the patient and physician-operator from the accumulation of saliva.

While these devices may be suitable for the particular purpose to which they address, they are not as suitable for increasing the speed and efficiency of an endoscopic procedure. It can be very difficult to maintain steady positioning of the various tubes (i.e. suction catheter, endoscope, etc.) necessary during an endoscopic procedure. Misdirecting or losing grip of the tubes during the procedure can greatly slow down the procedure and cause discomfort in the patient.

In these respects, the endoscopic bite block system according to the present invention substantially departs from the conventional concepts and designs of the prior art, and in so doing provides an apparatus primarily developed for the purpose of increasing the speed, efficiency and comfort of an endoscopic procedure.

BRIEF SUMMARY OF THE INVENTION

In view of the foregoing disadvantages inherent in the known types of medical instruments now present in the prior art, the present invention provides a new endoscopic bite block system construction wherein the same can be utilized for increasing the speed and efficiency of an endoscopic procedure.

The general purpose of the present invention, which will be described subsequently in greater detail, is to provide a new endoscopic bite block system that has many of the advantages of the medical instruments mentioned heretofore and many novel features that result in a new endoscopic bite block system which is not anticipated, rendered obvious, suggested, or even implied by any of the prior art medical instruments, either alone or in any combination thereof.

To attain this, the present invention generally comprises a base member including a central opening and at least one tube attachment, a channel member latitudinally extending from an outer edge of the central opening and a strap member removably attached to the base member, wherein the strap member removably attaches the base member to the mouth of the patient.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide an endoscopic bite block system that will overcome the shortcomings of the prior art devices.

A second object is to provide an endoscopic bite block system for increasing the speed and efficiency of an endoscopic procedure.

Another object is to provide an endoscopic bite block system that improves patient comfort during the endoscopic procedure.

An additional object is to provide an endoscopic bite block system that minimizes delays during the endoscopic procedure caused by displacement of the suction tubes.

A further object is to provide an endoscopic bite block system that allows the assistant to devote more attention to other required duties, such as but not limited to processing tissue sample obtained from the endoscope, administer intravenous sedation medication and monitor the patient's vital signs.

Another object is to provide an endoscopic bite block system that facilitates the application of continuous aspiration of saliva by maintaining stable, non hand-held attachment of the suction tube to the bite block.

Another object is to provide an endoscopic bite block system that allows the physician-operator to focus attention on duties, such as but not limited to identifying pathology, obtaining tissue samples via the endoscope and timely completion of the procedure rather than worrying about placement of the suction tubes.

Another object is to provide an endoscopic bite block system that efficiently secures the suction tube within the mouth of the patient.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
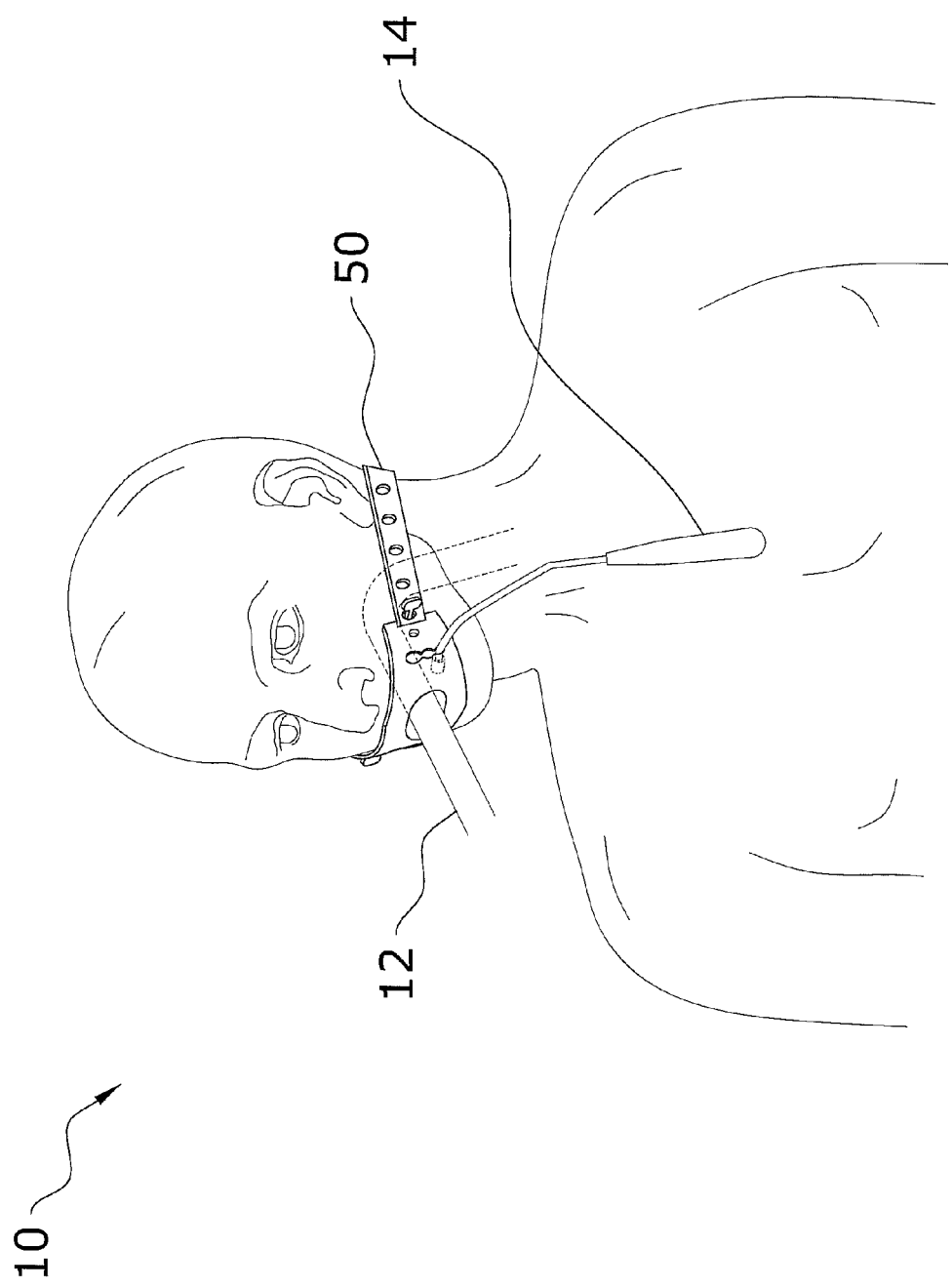
FIG. 1 is an upper perspective view of the present invention in use.

Turning now descriptively to the drawings, in which similar reference characters denote similar elements throughout the several views, FIGS. 1 through 5 illustrate an endoscopic bite block system 10, which comprises a base member 20 including a central opening 22 and at least one tube attachment, a channel member 30 latitudinally extending from an outer edge of the central opening 22 and a strap member 50 removably attached to the base member 20, wherein the strap member 50 removably attaches the base member 20 to the mouth of the patient.

B. Base Member

The base member 20 is preferably comprised of a configuration to fit over the mouth of a patient as illustrated in FIG. 1. The base member 20 is also preferably comprised of a plastic material; however other materials may be utilized in the construction of the base member 20, such as but not limited to a resilient and flexible material.

The base member 20 includes a central opening 22 as shown in FIGS. 1 through 5. The central opening 22 is preferably positioned in a substantially longitudinal and latitudinal center of the base member 20. The central opening 22 extends through the base member 20. The central opening 22 is preferably comprised of a substantially circular configuration; however the central opening 22 may be comprised of various other configurations, such as but not limited to rectangular and elliptical. An inner diameter of the central opening 22 is slightly greater than an outer diameter of an endoscope 12 as illustrated in FIG. 1.

The base member 20 also preferably includes at least one tube attachment. The tube attachment preferably attaches a suction tube 14 to the base member 20. The tube attachment also preferably includes a first tube attachment 24 and a second tube attachment 26 as shown in FIGS. 1 through 5. The first tube attachment 24 and the second tube attachment 26 preferably extend through the base member 20.

The first tube attachment 24 is preferably comprised of a slot configuration. The slot configuration of the first tube attachment 24 is preferably divided into several smaller circular configurations as shown in FIGS. 1 through 5. The width of the first tube attachment 24 also preferably descends in size from one end to an opposite end to accommodate various suction tube 14 diameters. It is appreciated that the first tube attachment 24 may be comprised of a plurality of separate circular configurations rather than the slot configuration. The first tube attachment 24 securely attaches the suction tubes 14 within the base member 20 so that the suction tubes 14 do not need to be held during the medical procedure.

The second tube attachment 26 is preferably comprised of a circular configuration to receive a separate tube than the first tube attachment 24 receives, wherein the first tube attachment 24 and the second tube attachment 26 are preferably utilized at different times. A diameter of the second tube attachment 26 is preferably substantially different than the various diameters of the first tube attachment 24 as illustrated in FIGS. 1 through 5. It is appreciated that the first tube attachment 24 and the second tube attachment 26 are on the same longitudinal side of the base member 20. It is also appreciated that during use the patient is rolled on a side wherein the first tube attachment 24 and the second tube attachment 26 are facing downward, wherein gravity assists in removing the saliva from the mouth of the patient.

Figure 3:
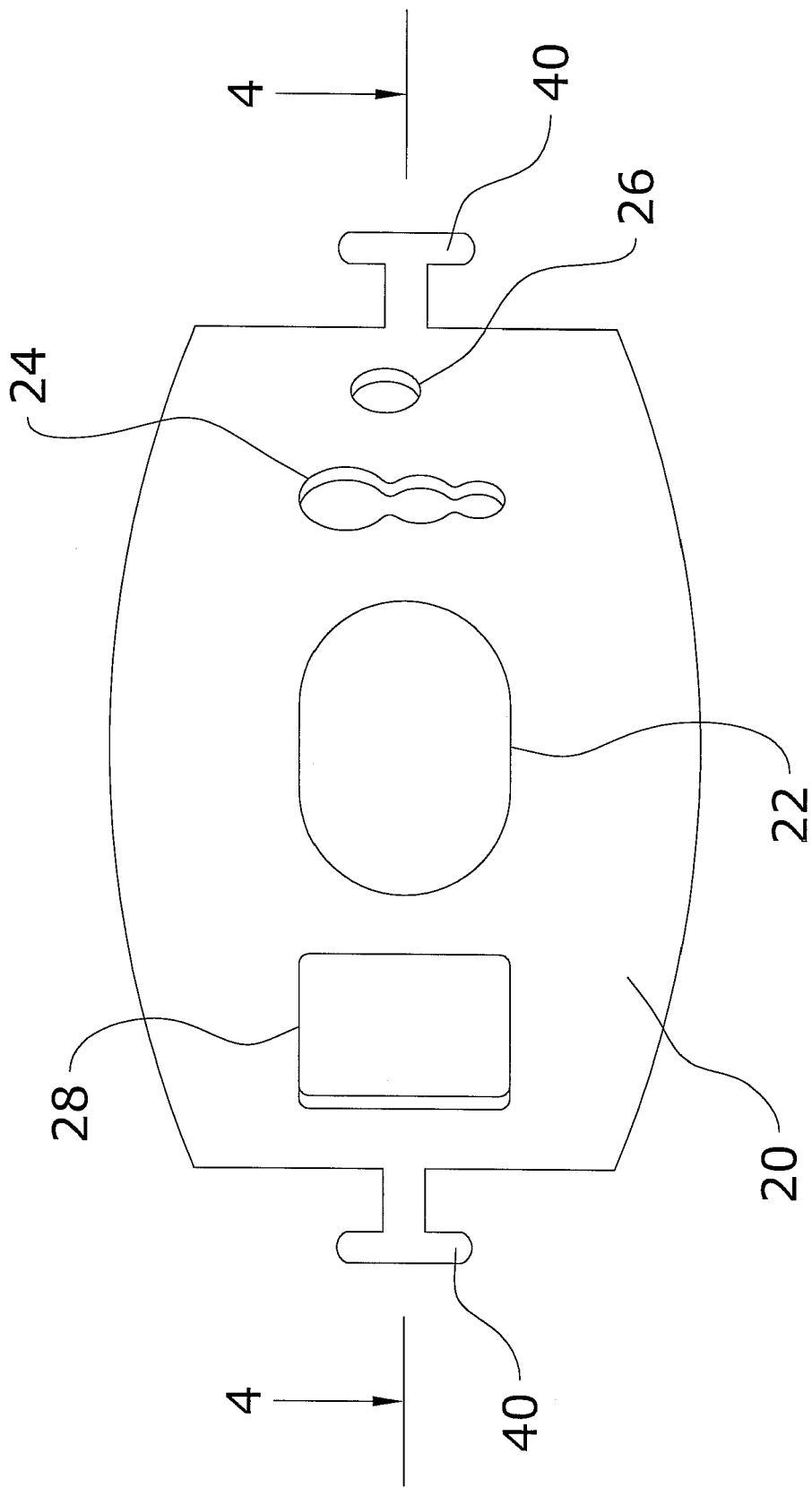
FIG. 3 is a front view of the base member.
Figure 4:
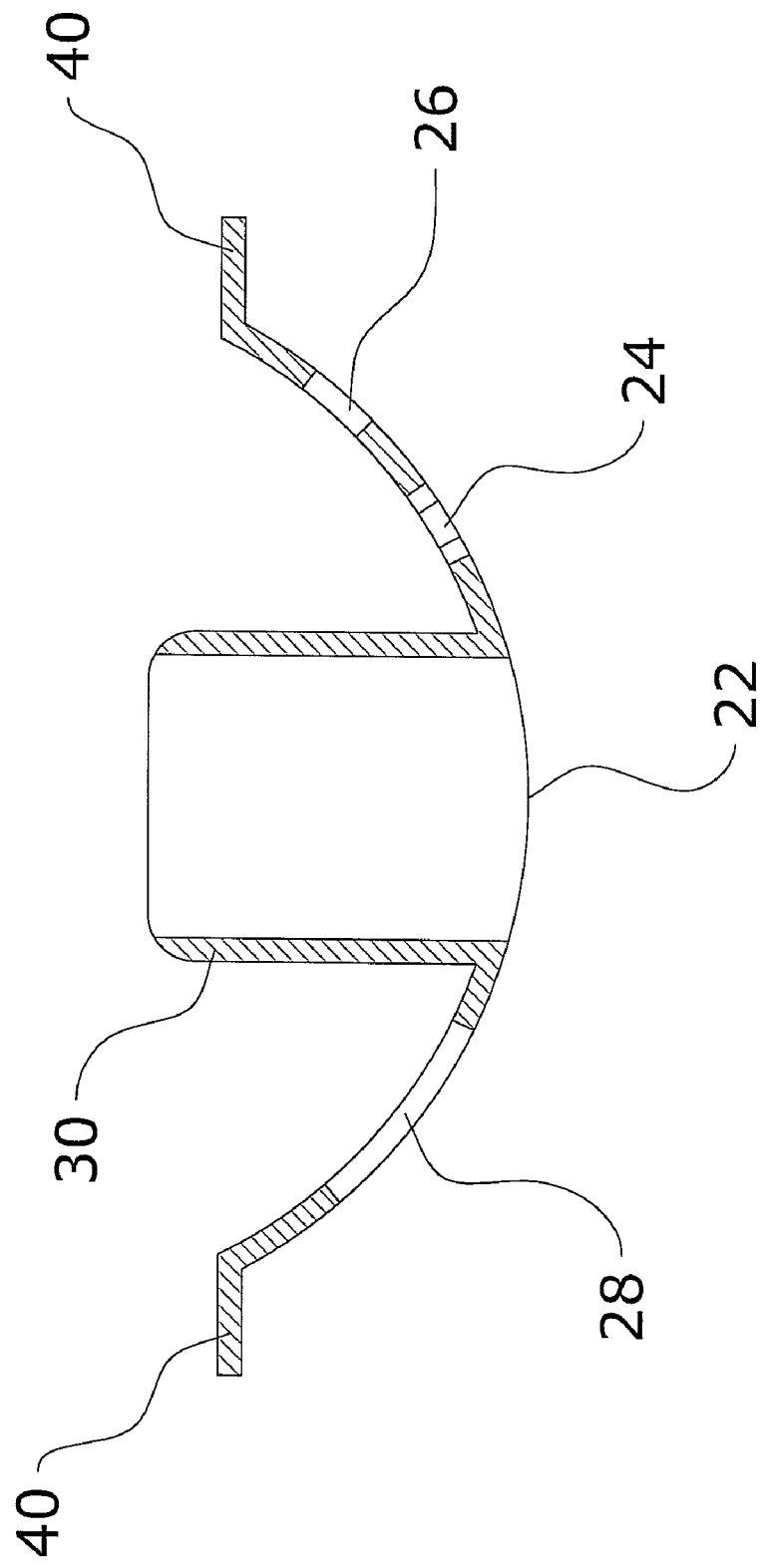
FIG. 4 is a sectional view taken along lines 4-4 of FIG. 3.
Figure 5:
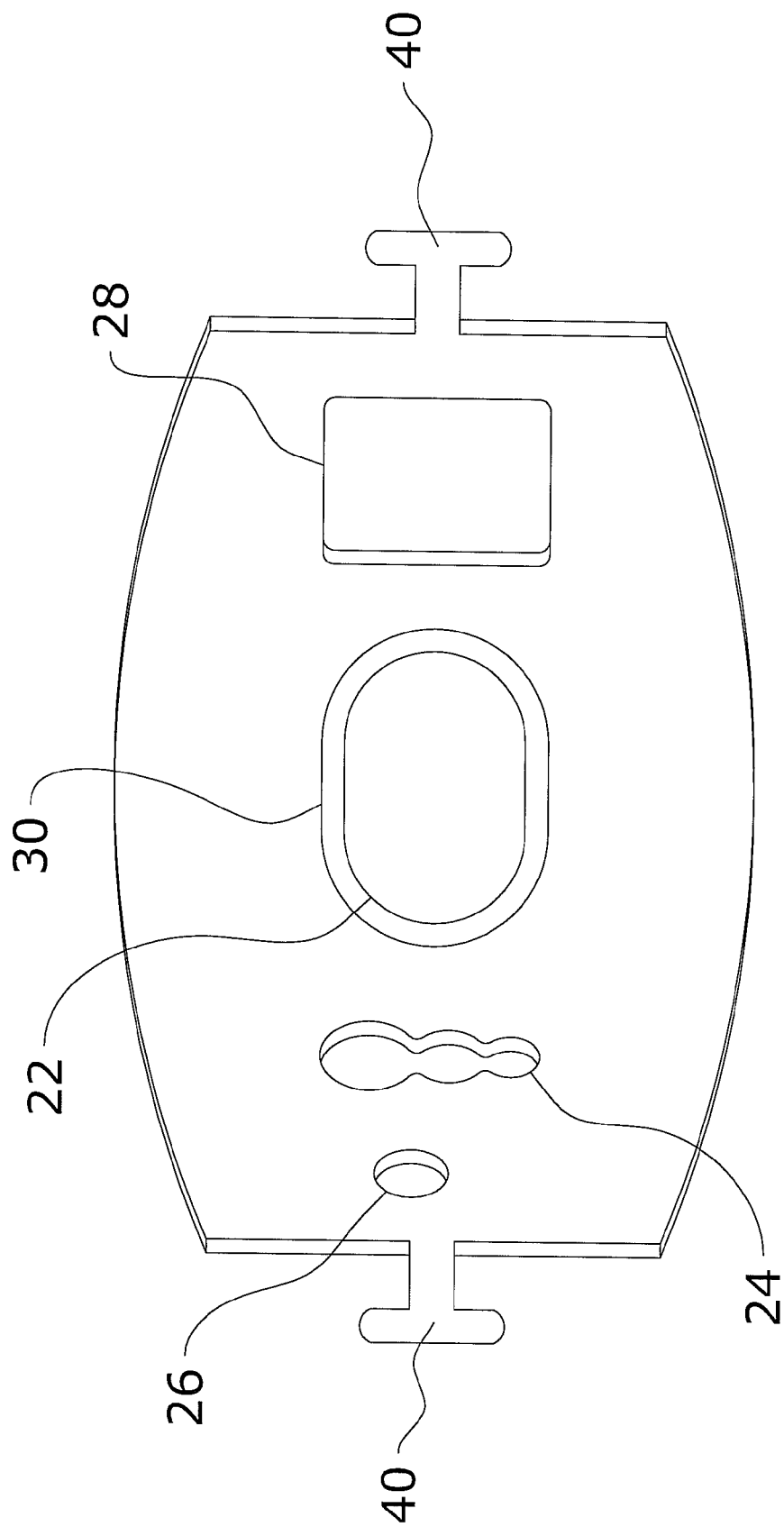
FIG. 5 is a rear view of the base member.

The base member 20 also preferably includes a side opening 28 as shown in FIGS. 3 through 5. The side opening 28 is preferably positioned on an opposite side of the base member 20 as the first tube attachment 24 and the second tube attachment 26. The side opening 28 extends through the base member 20. The side opening 28 is also preferably substantially similar or greater in size than the central opening 22 as shown in FIGS. 3 through 5. The side opening 28 provides an opening for the patient to breathe while the patient is utilizing the endoscopic bite block system 10.

C. Channel Member

The channel member 30 is preferably comprised of an elongated configuration as illustrated in FIG. 4. The channel member 30 is also preferably comprised of a circular configuration; however other configurations may be utilized in the construction of the channel member 30, such as but not limited to rectangular or elliptical. The channel member 30 is further preferably comprised of a hard material, such as but not limited to plastic. The hard material is necessary to prevent the patient from compressing or damaging the channel member 30 if the patient bites down on the channel member 30. Further, the channel member 30 is comprised of a hollow configuration to receive the endoscope 12.

The channel member 30 preferably extends latitudinally outward from an outer edge of the central opening 22. Further, the channel member 30 extends from an inner surface of the base member 20 as illustrated in FIG. 5. The channel member 30 is preferably integrally formed with the base member 20; however it is appreciated that the channel member 30 may be comprised of a separate structure than the base member 20.

D. Attachment Members

A pair of attachment members 40 preferably extend outwardly from opposite longitudinal ends of the base member 20 as shown in FIGS. 3 through 5. The attachment members 40 are preferably comprised of a similar material as the base member 20; however other materials may be utilized during construction of the attachment members 40.

The attachment members 40 are also preferably comprised of a T-shape configuration as illustrated in FIGS. 1 through 3 and 5. The attachment members 40 are preferably integrally formed with the base member 20; however it is appreciated that the attachment members 40 may be comprised of a separate structure than the base member 20.

E. Strap Member

Figure 2:
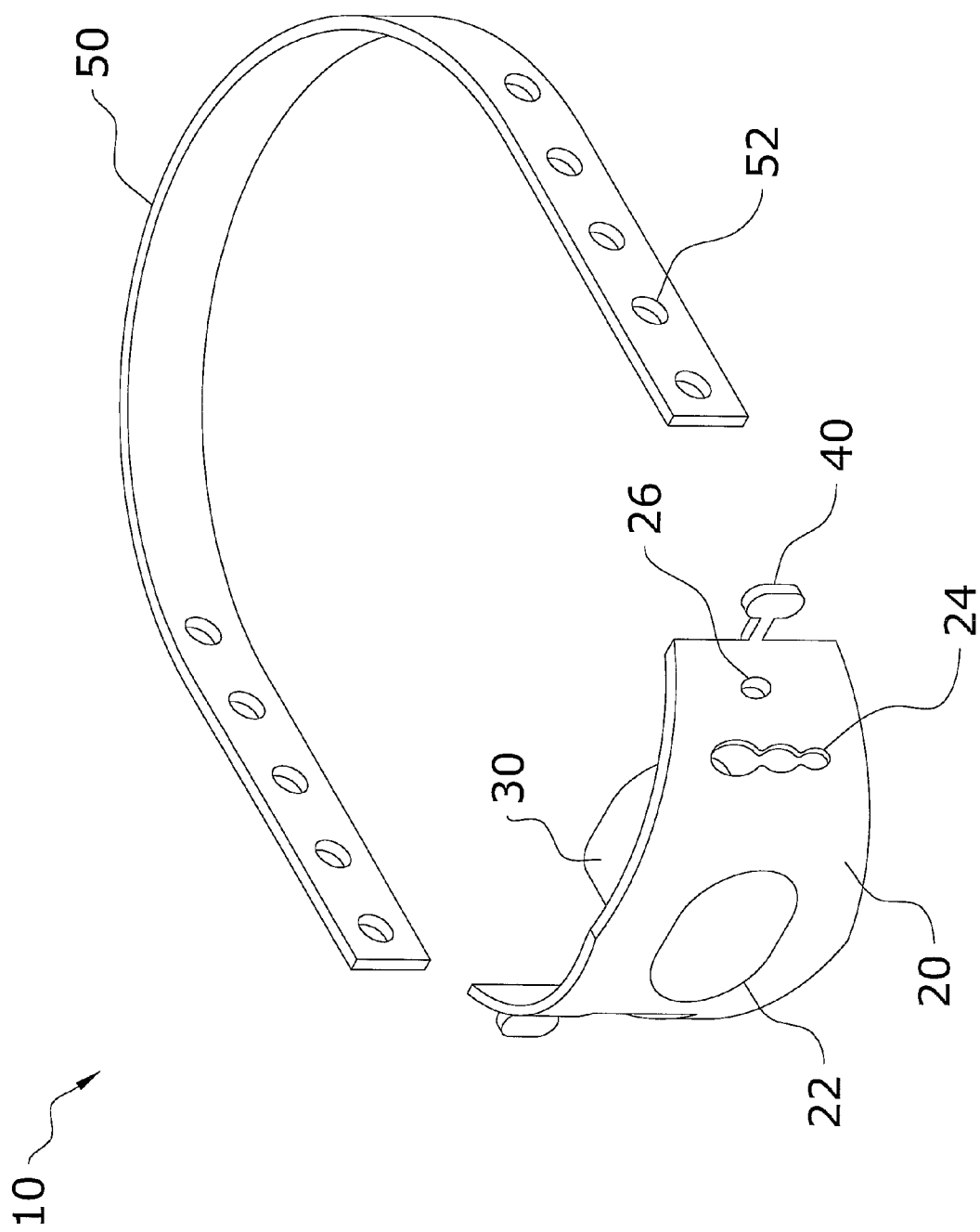
FIG. 2 is an exploded upper perspective view of the present invention.

The strap member 50 is preferably comprised of a flexible and resilient material, such as but not limited to rubber. The strap member 50 is also preferably comprised of an elongated configuration to fit around the head of a patient. The strap member 50 preferably includes a plurality of apertures 52 as shown in FIGS. 1 and 2.

The apertures 52 preferably allow the strap member 50 to removably attach to the attachment members 40 of the base member 20. The apertures 52 of the strap member 50 are preferably equally spaced throughout the strap member 50 to allow multiple lengths of the strap member 50 to be utilized with the base member 20.

F. In Use

In use, the base member 20 is first centered over the mouth of the patient and the channel member 30 is inserted into the mouth of the patient. The patient then bites down on the channel member 30 temporarily securing the base member 20 around the mouth of the patient. The strap member 50 is now removably attached to one of the attachment members 40 via an aperture 52 near an end of the strap member 50.

The strap member 50 may now be snugly wrapped around the back of the head of the patient and removably attached to an attachment member 40 on an opposite end of the base member 20 via another aperture 52. A suction tube 14 is now either secured within the first tube attachment 24 or the second tube attachment 26 depending on what diameter and what type of suction tube 14 is utilized.

The patient is ensured to be rolled on a side where the first tube attachment 24 and the second tube attachment 26 are facing downward, wherein gravity assists the suction tube 14 in removing saliva from the mouth of the patient. The endoscope 12 may now be inserted into the central opening 22 of the base member 20 and carefully guided within the interior of the patient. When the medical procedure is over, the endoscopic bite block system 10 is removed by simply reversing the above process.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

I claim:

1. An endoscopic bite block system, comprising:
   a base member including a central opening and at least one tube attachment, wherein said at least one tube attachment removably attaches a tube within said base member and wherein said base member is comprised of a configuration to fit over a mouth of a patient;
   wherein said at least one tube attachment includes a first tube attachment and a second tube attachment;
   wherein said first tube attachment is substantially comprised of a plurality of circular configurations;
   a channel member latitudinally extending from an outer edge of said central opening, wherein said channel member is hollow; and
   a strap member removably attached to said base member, wherein said strap member removably attaches said base member to said mouth of said patient.

2. The endoscopic bite block system of claim 1, wherein said at least one tube attachment extends through said base member.

3. The endoscopic bite block system of claim 1, wherein said second tube attachment is substantially comprised of a circular configuration.

4. The endoscopic bite block system of claim 1, wherein said plurality of circular configurations each substantially vary in diameter.

5. The endoscopic bite block system of claim 1, wherein said base member includes a side opening, wherein said side opening is positioned on an opposite longitudinal side as said at least one tube attachment.

6. The endoscopic bite block system of claim 1, wherein said channel member is comprised of an elongated configuration.

7. The endoscopic bite block system of claim 1, wherein said base member includes a pair of attachment members positioned on opposite longitudinal sides of said base member.

8. The endoscopic bite block system of claim 7, wherein said strap includes a plurality of apertures, wherein said plurality of apertures removably attach to said pair of attachment members of said base member.

9. An endoscopic bite block system, comprising:
   a base member including a central opening, a side opening and at least one tube attachment, wherein said base member is comprised of a configuration to fit over a mouth of a patient;
   wherein said at least one tube attachment removably attaches a tube within said base member and wherein said at least one tube attachment is substantially comprised of a plurality of circular configurations;
   wherein said side opening is positioned on an opposite longitudinal side as said at least one tube attachment;
   a channel member latitudinally extending from an outer edge of said central opening, wherein said channel member is hollow; and
   a strap member removably attached to said base member, wherein said strap member removably attaches said base member to said mouth of said patient.

10. The endoscopic bite block system of claim 9, wherein said at least one tube attachment extends through said base member.

11. The endoscopic bite block system of claim 9, wherein said at least one tube attachment includes a first tube attachment and a second tube attachment.

12. The endoscopic bite block system of claim 11, wherein said first tube attachment has said plurality of circular configurations and wherein said second tube attachment is substantially comprised of a circular configuration.

13. The endoscopic bite block system of claim 9, wherein said plurality of circular configurations each substantially vary in diameter.

14. The endoscopic bite block system of claim 9, wherein said channel member is comprised of an elongated configuration.

15. The endoscopic bite block system of claim 9, wherein said base member includes a pair of attachment members positioned on opposite longitudinal sides of said base member.

16. The endoscopic bite block system of claim 15, wherein said strap includes a plurality of apertures, wherein said plurality of apertures removably attach to said pair of attachment members of said base member.

17. An endoscopic bite block system, comprising:
- a base member having a flexible structure and adapted to fit over a mouth of a patient;
- wherein said base member has a central opening extending therethrough;
- wherein said base member includes a first tube attachment adapted to removably connect a tube to said base member;
- wherein said first tube attachment is comprised of a series of openings extending through a first side of said base member, wherein each of said series of openings have a circular configuration;
- a channel member extending rearwardly from an outer edge of said central opening, wherein said channel member is hollow; and
- a strap member removably attached to said first side and an opposite second side of said base member, wherein said strap member is adapted to wrap around a head of a patient.

18. The endoscopic bite block system of claim 17, wherein said series of openings vary in diameter.

19. The endoscopic bite block system of claim 18, wherein said series of openings are connected to each other.

20. The endoscopic bite block system of claim 17, wherein said base member includes a second tube attachment located on said first side of said base member and comprised of a circular opening extending through said base member, wherein said second tube attachment has a different diameter than any of said series of openings of said first tube attachment.

* * * * *